(12) United States Patent
McBurney et al.

(10) Patent No.: US 9,925,352 B2
(45) Date of Patent: Mar. 27, 2018

(54) METHOD FOR MAKING A READY-TO-USE CATHETER ASSEMBLY AND READY-TO-USE-CATHETER ASSEMBLY

(71) Applicant: Willy Rusch GmbH, Kernen-Rommelshausen (DE)

(72) Inventors: Denzell McBurney, Moate (IE); Morgan Tierney, Tullamore (IE); Ronald John Kelly, Oranmore (IE)

(73) Assignee: WILLY RUSCH GMBH, Kernen-Rommelshausen (DE)

( * ) Notice: Subject to any disclaimer, the term of this patent is extended or adjusted under 35 U.S.C. 154(b) by 361 days.

(21) Appl. No.: 14/481,420

(22) Filed: Sep. 9, 2014

(65) Prior Publication Data
US 2015/0068927 A1   Mar. 12, 2015

(30) Foreign Application Priority Data
Sep. 10, 2013  (EP) ..................................... 13004403

(51) Int. Cl.
*A61M 25/00*  (2006.01)
*A61L 2/08*  (2006.01)
(Continued)

(52) U.S. Cl.
CPC ............. *A61M 25/002* (2013.01); *A61L 2/08* (2013.01); *A61M 25/0017* (2013.01);
(Continued)

(58) Field of Classification Search
CPC ......................... A61M 25/002; A61M 25/0017
(Continued)

(56) References Cited

U.S. PATENT DOCUMENTS 6,059,107 A * 5/2000 Nøsted .................. A61L 29/085
 206/210
6,848,574 B1 * 2/2005 Israelsson ........... A61M 25/002
 206/210

(Continued)

FOREIGN PATENT DOCUMENTS

EP   2060296 A1   5/2009
EP   2389972 A1   11/2011
(Continued)

*Primary Examiner* — Gloria R Weeks
(74) *Attorney, Agent, or Firm* — Baker & Hostetler LLP

(57) ABSTRACT

A method of making a ready-to-use catheter assembly and a ready-to-use catheter are provided, which avoids any degradation of the catheter during sterilization. The method comprises: placing a catheter with a hydrophilic coating and a wetting fluid in a catheter package made of low moisture transmission material while the package is in a first condition wherein an insertable length of the hydrophilic coating of the catheter is not in contact with the wetting fluid, sterilizing the catheter package with the catheter and the wetting fluid by radiation sterilization while the catheter package is kept in a condition in which the insertable length is not in contact with the wetting fluid, transferring the catheter package with the catheter and the wetting fluid into a second condition, bringing the wetting fluid into contact with at least the insertable length and activating the insertable length via gravity and/or via inertia.

10 Claims, 4 Drawing Sheets

(51) Int. Cl.
  *B65B 55/08*   (2006.01)
  *A61M 25/06*   (2006.01)
(52) U.S. Cl.
  CPC ........... *B65B 55/08* (2013.01); *A61L 2202/24* (2013.01); *A61M 2025/0046* (2013.01); *A61M 2025/0681* (2013.01)
(58) Field of Classification Search
  USPC ..................... 206/364; 53/425, 431; 604/265
  See application file for complete search history.

(56) References Cited

U.S. PATENT DOCUMENTS

| | | | |
|---|---|---|---|
| 8,523,843 B2* | 9/2013 | Kavanagh | A61M 25/002 206/364 |
| 9,028,858 B2* | 5/2015 | Nielsen | A61L 29/085 206/364 |
| 2001/0001443 A1 | 5/2001 | Kayerod et al. | |
| 2009/0200187 A1* | 8/2009 | Nestenborg | A61M 25/002 206/364 |
| 2010/0258568 A1* | 10/2010 | Frederiksen | A61M 25/002 220/502 |
| 2011/0114520 A1* | 5/2011 | Matthison-Hansen | A61M 25/002 206/364 |
| 2013/0153446 A1* | 6/2013 | Utas | B65B 7/00 206/210 |
| 2015/0273180 A1* | 10/2015 | Schonfeldt | A61M 25/0017 206/210 |
| 2015/0335856 A1* | 11/2015 | Utas | A61M 25/002 206/210 |

FOREIGN PATENT DOCUMENTS

| | | |
|---|---|---|
| WO | WO1998011932 | 3/1998 |
| WO | WO1999003677 | 1/1999 |
| WO | 03092779 A1 | 11/2003 |
| WO | 2004075944 A2 | 9/2004 |
| WO | 2009140971 A1 | 11/2009 |

* cited by examiner

METHOD FOR MAKING A READY-TO-USE CATHETER ASSEMBLY AND READY-TO-USE-CATHETER ASSEMBLY

CROSS-REFERENCE TO RELATED APPLICATION

This application claims priority to foreign European Patent Application EP 13004403.5, filed on Sep. 10, 2013, the disclosure of which is incorporated herein by reference in its entirety.

FIELD OF THE INVENTION

The present patent application refers to a method of making a ready-to-use catheter assembly and to a ready-to-use catheter assembly made according to this method.

BACKGROUND

Such ready-to-use catheter assemblies are usually used for intermittent catheterization by persons who are able to do so without the assistance of a healthcare professional. An important feature of such catheters is the ability of the catheter to slide easily through the urethra without exposing the urethral walls to any risk of damage. Therefore, lubricated catheters are known which utilize a gel that is applied to the outer surface of the catheter tube prior to insertion into the urethra. Furthermore, hydrophilic coated catheters are known wherein a hydrophilic coating on the catheter tube is activated prior to use by means of a wetting fluid, for example, water or saline solution.

In order to reduce the risk of infection when performing intermittent catheterization of the bladder, the catheter assembly needs to be as clean and antiseptic as possible. Therefore, the catheter assembly is sterilized before use. A typical method used for sterilization of catheter assemblies is radiation sterilization. However, during radiation sterilization of water containing materials, for example, an activated hydrophilic coating of a catheter, the water produces radicals which often induce unwanted changes within the material. In the case of activated hydrophilic coatings, the coating performance is often reduced, i.e. lubricity and dry out time of the catheter assembly are negatively affected. This effect on performance results from the reduction in coating constituents' molecular weight and/or through additional cross-linking of the coating.

EP 2 060 296 A1 already shows a ready-to-use catheter assembly wherein an activated catheter is provided in a catheter package. The catheter assembly comprises a catheter package which is divided into a first cavity and a second cavity by a gas permeable, liquid impermeable barrier. The first cavity accommodates a hydrophilic coated catheter, the second cavity accommodates a quantity of wetting liquid in its liquid phase. The catheter assembly is sterilized shortly after placing the catheter and the wetting liquid in the package. Prior to use, the liquid in the second cavity changes phase into vapor, the vapor passes the gas permeable barrier between the liquid and the hydrophilic coated catheter and activates the hydrophilic coating of the catheter. However, the time needed for activating the catheter is relatively long and may amount to 6 weeks.

Another ready-to-use catheter assembly is known from Document U.S. 2001/0001443 A1. This document shows a ready-to-use catheter assembly comprising a urinary catheter with a hydrophilic coating and a catheter package with a cavity for accommodation of the catheter. The catheter package is made up of a gas impermeable material and accommodates a wetting liquid for activating the hydrophilic coating of the catheter. The wetting liquid is preferably contained in a spongy material.

SUMMARY OF THE INVENTION

It is the object of the present patent application to provide a further method of making a ready-to-use catheter assembly and to provide a ready-to-use catheter assembly which overcomes at least partially the disadvantages of the devices known so far.

The method therefore comprises the following steps:

Placing a catheter with a hydrophilic coating and a wetting fluid in a catheter package made of a material with low moisture transmission while the package is in a first condition wherein at least an insertable length of the hydrophilic coating of the catheter is not in contact with the wetting fluid;

Sterilizing the catheter package with the catheter and the wetting fluid by means of radiation sterilization while the catheter package is kept in a condition in which at least the insertable length of the hydrophilic coating of the catheter is not in contact with the wetting fluid;

Transferring the catheter package with the catheter and the wetting fluid into a second condition, thereby bringing the wetting fluid into contact with at least the insertable length of the hydrophilic coating of the catheter, and activating at least the insertable length of the hydrophilic coating of the catheter via gravity and/or inertia.

In the context of this document, the term "gravity" also comprises artificially induced forces, i.e. centrifugal forces. Low moisture transmission means that the material of the catheter package keeps the wetting fluid in the catheter package for at least the shelf life of the ready-to-use catheter assembly, so that the catheter remains activated for the complete shelf life. Usually the shelf life lies in a range of 36 month to 5 years.

During radiation sterilization, the hydrophilic coating of the catheter and the wetting fluid are kept separate, so that any degradation of the quality of the hydrophilic coating and therewith of the lubricity of the ready-to-use catheter is avoided. Furthermore, as the activation of the catheter is carried out in a short time, it is not necessary to allow the aging of the catheter before use.

In a preferred variant, the catheter and the wetting fluid are arranged in the catheter package in such a way that there is free flow communication between the catheter and the wetting fluid. Therefore, when changing the condition of the catheter package from the first condition to the second condition, the wetting fluid can flow to the hydrophilic coating of the catheter without being disturbed by any obstacles. An easy activation of the catheter is guaranteed.

In a further preferred variant, activating the hydrophilic coating of the catheter is performed after sterilizing the catheter assembly and before shipment to the end-user. The activation of the catheter therefore is part of the manufacturing process of the ready-to-use catheter assembly, the catheter assembly is delivered to the user in a ready-to-use form, the user must not activate the catheter but can use it immediately.

In yet another variant of the method, at least the insertable length of the hydrophilic coating of the catheter and the wetting fluid are separated via the force of gravity when in the first condition. This is a very simple method to obtain a secure separation between at least the insertable length of the hydrophilic coating of the catheter and the wetting fluid, which ensures that the hydrophilic coating is not damaged during radiation sterilization.

Furthermore, it can be provided that at least the insertable length of the hydrophilic coating of the catheter is activated by turning the package with the wetting fluid and the catheter with the hydrophilic coating around an angle of at least 90°. This is a very simple way to bring the wetting fluid into contact with the hydrophilic coating of the catheter and thereby activating the hydrophilic coating of the catheter.

In still another variant of the method, a compartment for the wetting fluid is arranged in the catheter package which is in direct fluid communication with the hydrophilic coating of the catheter. It is thereby ensured that the wetting fluid is not accidentally brought into contact with a hydrophilic coating before the radiation sterilization of the catheter assembly.

In still another variant of the method, at least the hydrophilic coating of the catheter is surrounded by a sleeve which is combined with the compartment for the wetting fluid and directs the wetting fluid from the compartment to the hydrophilic coating. In this case, only a very small amount of wetting fluid is needed for activating the catheter because it is directly led to the hydrophilic coated part of the catheter. There is no superfluous liquid in the catheter package which may spill when the package is opened.

In case of the ready-to-use catheter assembly, the above mentioned object is solved by a ready-to-use catheter assembly comprising a catheter package made of a material with low moisture transmission and a catheter with an activated hydrophilic coating, the coating being activated by a wetting fluid, the catheter being arranged in the package, wherein the package has two regions which are designed so as to store the wetting fluid and at least an insertable length of the hydrophilic coating of the catheter separated from each other in a first condition of the catheter package, to bring the wetting fluid and the hydrophilic coating of the catheter together in a second condition and to allow free flow communication between the first region and the second region through changing over from the first condition into the second condition via gravity and/or inertia only. Due to this construction of the ready-to-use catheter assembly, it is possible to provide a catheter in a ready-to-use form which does not have to be activated by a user and which does not experience any degradation during radiation sterilization. So far, catheter assemblies are known which comprise a catheter package, a hydrophilic coated catheter and a sachet with wetting fluid, wherein the catheter and the sachet with the wetting fluid are arranged in the catheter package. In order to activate the hydrophilic coating of the catheter, a pressure is exerted on the sachet so that the sachet bursts open and the wetting fluid is delivered in the catheter package. As shown above, the force which is necessary to open the sachet and to activate the hydrophilic coating of the catheter is a compressive force.

In a further embodiment, the first region of the catheter package is formed by a compartment for the wetting fluid which is connected to the second region of the catheter package via a free flow opening. With this construction, a free flow communication between the wetting fluid and the hydrophilic coating of the catheter for activating the catheter is possible, however, the risk of spillage of the wetting fluid before sterilization of the catheter assembly is minimized.

It can further be provided that the compartment for the wetting fluid is separated from the second region of the catheter package via a bridge which comprises the free flow opening. The bridge can be easily realized for example as a welding seam in the catheter package so that an easy manufacturing of the catheter assembly is possible.

However, it can also be provided that the compartment for the wetting fluid has a tube-like shape and is arranged near a tip of the hydrophilic coated catheter. The wetting fluid is then directed to the catheter when activating the hydrophilic part of the catheter which helps in reducing the amount of wetting fluid needed.

The amount of wetting fluid needed can further be reduced when the catheter is surrounded by a sleeve which is combined with the free flow opening of the tube-like shaped compartment and which sleeve directs the wetting fluid to the hydrophilic coating of the catheter when the assembly is in the second condition, in which at least the insertable length of the hydrophilic coating of the catheter is activated.

In yet another embodiment, the sleeve can comprise an insertion aid which is combined with the tube-like shaped compartment. This construction also helps in reducing the amount of wetting fluid needed.

BRIEF DESCRIPTION OF THE DRAWINGS

In the following the invention is described in more detail with the aid of drawings:

FIGS. 1b-e show the transfer of the ready-to-use catheter assembly of FIG. 1a from the first condition into a second condition.

DETAILED DESCRIPTION

Figure 1:
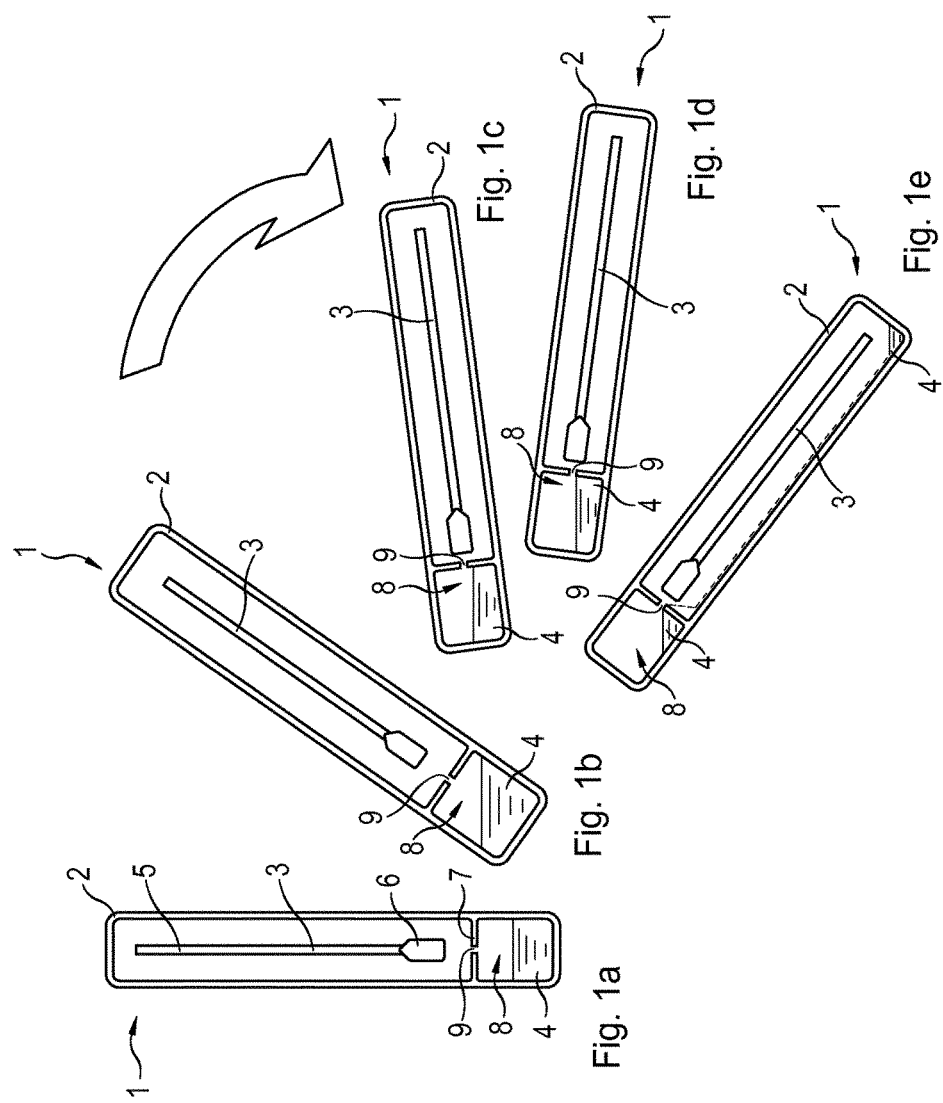
FIG. 1 a shows a first embodiment of a ready-to-use catheter assembly in a first condition.

FIG. 1a shows a first embodiment of a ready-to-use catheter assembly 1. The ready-to-use catheter assembly 1 comprises a catheter package 2, a catheter 3 arranged in the catheter package 2 and a wetting fluid 4 which is also arranged in the catheter package 2. The catheter package 2 is made of a material that has a low moisture transmission such that the wetting fluid 4 is retained within the package 2. Examples for such materials with low moisture transmission are multi-layered polymeric films and aluminum foils. Due to the use of these materials, the wetting fluid is retained within the package for a time span of up to five years and typically 36 months. It is thus ensured that the ready-to-use catheter assembly has a suitable product shelf life. Furthermore, due to the very low moisture transmission of the package material, the amount of wetting fluid 4 needed can be minimized, because nearly no wetting fluid can escape from the package. As there is only a small amount of wetting fluid in the package, the risk of spillage when opening the package is reduced.

The catheter 3 comprises a catheter tube 5 and a catheter funnel 6. The ready-to-use catheter assembly 1 is preferably used for intermittent catheterization. In order to allow an easy catheterization, the surface of the catheter tube 5 which is inserted in the urethra, this is the insertable length, should have a high lubricity. Therefore, at least a part of the catheter tube 5 is coated with a hydrophilic coating. In the context of this document the hydrophilic coated parts of the catheter are referred to as hydrophilic coating. The hydrophilic coating of the catheter 3, that means the catheter tube 5, must be activated before use to ensure the high lubricity of the catheter tube 5. The activation is carried out by bringing the catheter 3 and especially the hydrophilic coating the catheter 3 in contact with the wetting fluid 4.

It is known that during radiation sterilization of the catheter assembly, the coating performance of an activated hydrophilic coating is reduced such that lubricity and dry out time are negatively affected. Therefore, the catheter package 2 comprises a bridge 7 which separates the lower part, the first region of the catheter package 2, from the remaining part of the catheter package 2, the second region, and forms a compartment 8 for the wetting fluid 4. The bridge 7 does not completely separate the first region, that is the compartment 8, from the second region of the catheter package 2 but comprises a free flow opening 9. Due to this free flow opening 9, a free flow communication between the catheter 3 and the wetting fluid 4 is realized in the package 2. The bridge 7 can for example be formed by a welding seam.

FIG. 1a shows the catheter assembly 1 in a first condition, wherein the compartment 8 with the wetting fluid 4 is arranged beneath the catheter 3. In this embodiment, the different conditions of the catheter assembly 1 correspond to different positions of the catheter assembly 1. Therefore, the wetting fluid 4 is kept in the first region of the package via gravity and a secure separation between the hydrophilic coating of the catheter 3 and the wetting fluid 4 is realized. Therefore, when sterilizing the ready-to-use catheter assembly in this first condition, i.e. the first position, a contact between the wetting fluid 4 and the catheter 3 is avoided and any degradation of the hydrophilic coating of the catheter 3 is prevented.

Figure 2:
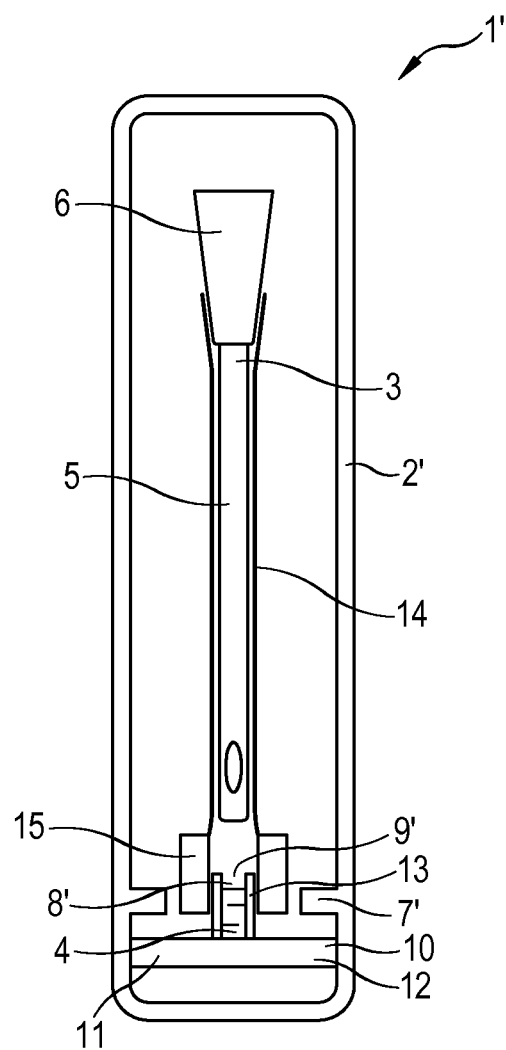
FIG. 2 shows a second embodiment of the ready-to-use catheter assembly.

FIG. 2 shows a second embodiment of a ready-to-use catheter assembly 1'. This catheter assembly 1' basically corresponds to the catheter assembly as already described. For the same parts, the same reference numbers are used. In the following, the differences are described.

The ready-to-use catheter assembly 1' also comprises a catheter package 2', a catheter 3 which is arranged in the catheter package 2' and a wetting fluid 4, which is also arranged in the catheter package 2'. The catheter package 2' is made of a material with low moisture transmission as described above. Furthermore, an element 10 is arranged in the package 2'. The element 10 has the shape of a T and is called T-piece. The two arms of the T are connected to the package 2' in order to fix the element 10 in the package 2'. The leg of the T 13 is hollow and forms the compartment 8' for the wetting fluid 4. In FIG. 2, the ready-to-use catheter assembly 1' is shown in a first condition which is maintained before and during sterilization. In this first condition, the wetting fluid 4 is arranged in the compartment 8' and is therefore kept separate from the catheter 3 and the hydrophilic coating of the catheter 3. The end of the compartment 8' is open, so that the wetting fluid 4 is in free flow communication with the catheter 3. Therefore, the open end of the compartment 8' also forms a free flow opening 9'. Also in this embodiment the different conditions of the catheter assembly 1' correspond to different positions.

The catheter 3 also comprises a catheter tube 5 and a catheter funnel 6. Near the tip of the catheter tube, the catheter tube 5 is provided with drainage eyes. At least parts of the catheter tube 5 are coated with a hydrophilic coating. The catheter tube 5 is surrounded by a sleeve 14. The sleeve 14 completely covers the catheter tube 5 so that the catheter tube 5 is not touched by a user when inserting the catheter in the urethra and the catheter is therefore kept antiseptic. At the end of the sleeve 14 facing the tip of the catheter tube 5, an insertion aid 15 is connected to the sleeve 14. This insertion aid 15 facilitates the insertion of the catheter tube 5 in the urethra of a user. The insertion aid 15 has the form of a short tube. The inner diameter of the insertion aid 15 is larger than the outer diameter of the leg of the T shaped element 10. The insertion aid 15 is slipped onto the leg 13 of the T shaped element 10 and therefore surrounds the compartment 8' for the wetting fluid 4.

The package 2' is provided with a small bridge 7' which has an opening which surrounds the compartment 8' and the insertion aid 15 slipped onto the compartment 8'. The bridge 7' helps in keeping the T shaped element 10 in the right position.

In the following, the method for making the ready-to-use catheter assembly is described for the first embodiment of the ready-to-use catheter assembly 1 with the FIGS. 1a to 1e.

In FIG. 1a, the ready-to-use catheter assembly 1 is shown in a first condition, i.e. a first position of the catheter package 2. In this position, the wetting fluid 4 is arranged at the bottom of the catheter package, the first region, and the catheter 3 with the hydrophilic coating is arranged above the wetting fluid 4. Therefore, the hydrophilic coating of the catheter 3 does not come into contact with the wetting fluid 4. The ready-to-use catheter assembly 1 is then sterilized via radiation sterilization, for example, by means of gamma radiation while keeping the catheter package 2 in a condition, i.e. a position, in which the hydrophilic coating of the catheter 3 and the wetting fluid 4 are separated from each other. In this way, it can be ensured that the wetting fluid 4 does not come into contact with the hydrophilic coating of the catheter 3 during the sterilization process of the catheter assembly 1. A degradation of the hydrophilic coating of the catheter 3 can thus be avoided. This position is maintained until radiation sterilization is completed.

After radiation sterilization is completed, the ready-to-use catheter assembly 1 is rotated as can be seen in FIGS. 1b, 1c, 1d and 1e. When rotating the ready-to-use catheter assembly 1, the catheter package 2 is turned and brought in a second condition so that the compartment with the wetting fluid is arranged above the catheter 3. Due to gravity, the wetting fluid 4 changes its position in the compartment 8 and reaches the free flow opening 9. The wetting fluid 4 then flows through the free flow opening 9 of the bridge 7 and comes into contact with the catheter 3. Thereby, the hydrophilic coating of the catheter 3 is activated. As the activation of the catheter 3, that means the hydrophilic coating of the catheter 3, takes place after the radiation sterilization of the ready-to-use catheter assembly 1, a degradation of the hydrophilic coating of the catheter 3 and thereby of the lubricity of the catheter 3 is minimized.

In the following, the method of making a ready-to-use catheter assembly is explained with regard to the second embodiment for a ready-to-use catheter assembly 1' using FIGS. 2, 3 and 4.

FIG. 2 shows the ready-to-use catheter assembly 1' in the first condition, i.e. first position of the catheter package 2'. In the first position, the catheter package 2' is arranged in such a way that the wetting fluid 4 is kept in the compartment 8' and is arranged below the catheter 3 with the hydrophilic coating. The catheter 3 and its hydrophilic coating are kept separate from the wetting fluid 4 via gravity. This position is maintained during the radiation sterilization of the ready-to-use catheter assembly 1'. The sterilization is preferably carried out with gamma radiation.

Figure 3:
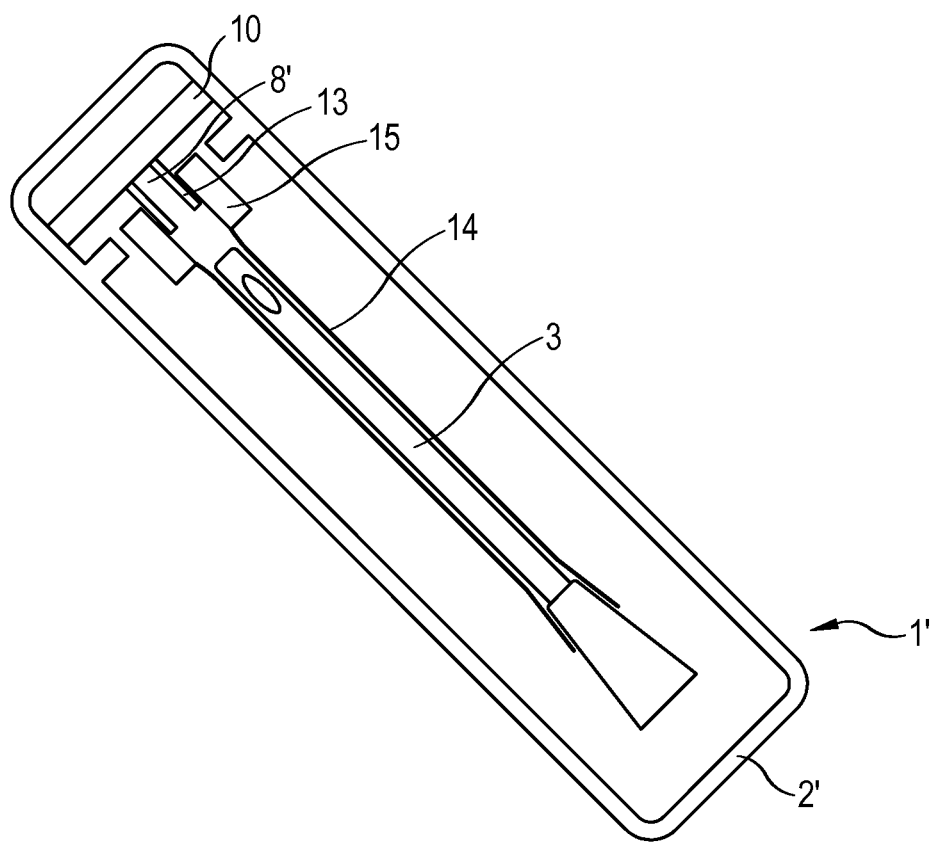
FIG. 3 shows the ready-to-use catheter assembly of FIG. 2 in a second condition and, FIG. 4 shows the ready-to-use catheter assembly of FIG. 2 shortly before use.

FIG. 3 shows the step of activating the ready-to-use catheter assembly 1'. After sterilization, the catheter package 2' is turned around an angle of at least 90°, and brought in a second condition, i.e. a second position so that the wetting fluid 4 flows from the compartment 8' through the introduction aid 15 into the sleeve 14 surrounding the catheter 3. The wetting fluid 4 is thereby brought into contact with at least the insertable length of the hydrophilic coating of the catheter 3 and activates at least the insertable length of the hydrophilic coating. The wetting fluid 4 is preferably a saline solution or water. Due to the use of the sleeve 14 which surrounds the catheter 3, only a small amount of wetting fluid is needed for activating the hydrophilic coating of the catheter. Due to this small amount of wetting fluid 4, nearly no free wetting fluid is left in the catheter package 2' after the activation of the catheter 3. Therefore, the risk of spillage when opening the catheter package 2' is minimized.

After the activation of the hydrophilic coating of the catheter 3 with the wetting fluid 4, the catheter is in the ready-to-use condition. This means, that the whole catheter assembly 1' is delivered to the user in such a form that it can be directly used. The user does not have to undertake any steps to activate the catheter 3 but only has to open the package 2 to pull the activated catheter 3 with the sleeve 14 and the insertion aid 15 from the catheter package 2' and can start with the intermittent catheterization.

Figure 4:
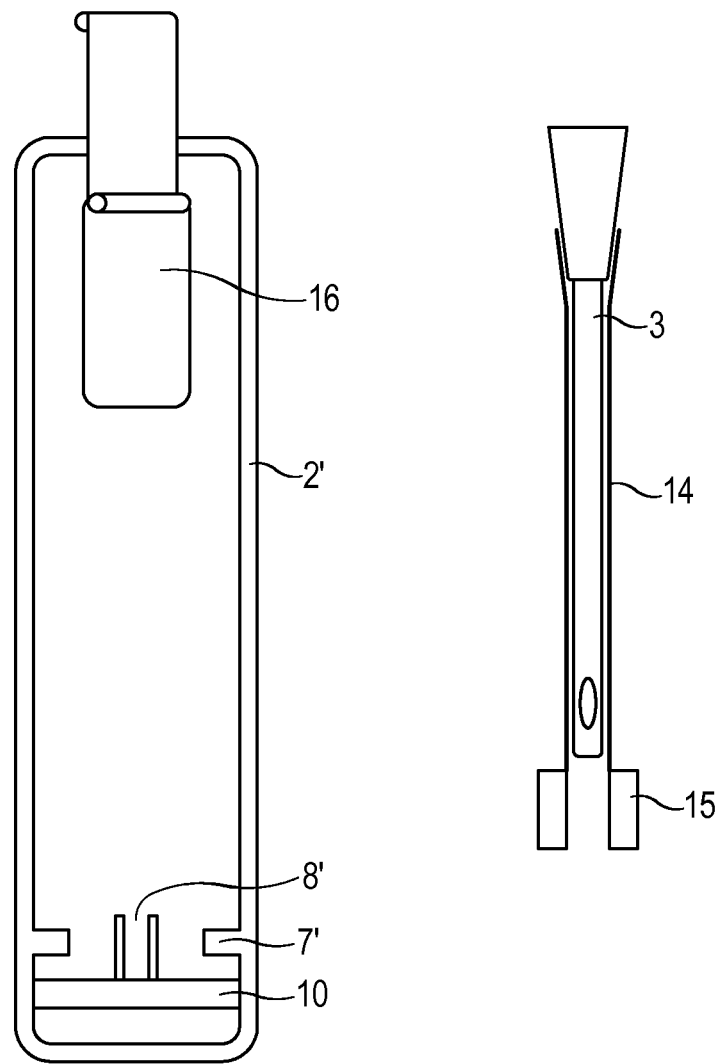

This is shown in FIG. 4. The catheter package 2' is preferably provided with an opening 16 which can be easily opened and through which the user can pull out the activated catheter 3. The sleeve 14 remains on the catheter 3 when taking the catheter 3 out of the package 2'. The user then only touches the sleeve 14, the catheter 3, especially the catheter tube 5 which is inserted in the urethra of the user, is kept in an antiseptic state.

The orientation of the catheter package 2, 2' from packaging to product release can be monitored using tiled indicators. In this way, it can be tracked if the process for making the ready-to-use catheter assembly has been executed without errors. As can be seen in FIG. 4 of the second embodiment for the ready-to-use catheter assembly 1', the catheter package 2' is turned back in an upright position before pulling out the catheter 3. Excess wetting fluid can then return to the compartment 8' when the user takes the ready-to-use catheter assembly to open it. This helps to reduce the likelihood of spilling wetting fluid during the opening of the catheter package 2 and product use. The same applies for the catheter assembly 1 shown in FIGS. 1a to 1e.

Furthermore, it is pointed out that the wetting fluid can be directly loaded into the catheter package without providing a bridge or a compartment.

The transfer of the wetting agent may also be via the catheter inner lumen. In this approach, the catheter funnel and catheter drainage eyes may be used as the bridge for the wetting agent. The wetting fluid may also be included within a chamber in the catheter, and the catheter inner lumen or an insertion or handling aid.

In addition to gravity, the use of centrifugal forces may also be employed to ensure that the wetting fluid is transferred to the hydrophilic coated parts of the catheter. Furthermore, sudden linear displacement of a product (Newton's First Law of Motion) can also be used to transfer the wetting fluid to the hydrophilic coating of the catheter. The inertia of the wetting fluid will resist the change in motion and stay stationary relative to the product. When the product decelerates or stops suddenly, the wetting fluid will again resist this change in motion in its own state of motion (keeps flowing). This is a further mechanism of moving the wetting fluid from one place to another relative to the product and can act as a mechanism of activation based on inertia force of the wetting fluid and its resistance to change of motion.

As already described above, the catheter assembly is delivered to the end user in a ready-to-use condition. This means, the activation of the hydrophilic coating of the catheter is part of the method of making the ready-to-use catheter assembly. Therefore, activation of the hydrophilic coated parts of the catheter is performed at any time between sterilization of the catheter assembly and shipment to the end-user.

The catheter package 2, 2' is made of a material with low moisture transmission, for example, multilayer polymeric films or aluminum foils. Therefore, the wetting fluid is retained within the package for a time span of up to five years and typically 36 months. It is thus ensured that the ready-to-use catheter assembly has a suitable product shelf life.

REFERENCE NUMBERS 1, 1': Ready-to-use catheter assembly
2, 2': Catheter package
3: Catheter
4: Wetting fluid
5: Catheter tube
6: Catheter funnel
7, 7': Bride
8, 8': Compartment
9: Free flow opening
10: T-shaped element
11, 12: Arms of T-shaped element
13: Leg of T-shaped element
14: Sleeve
15: Insertion aid
16: Opening

The invention claimed is:

1. A method of making a ready-to-use catheter assembly, comprising:
   placing a catheter with a hydrophilic coating and a wetting fluid in a catheter package made of a material with low moisture transmission while the catheter package is in a first condition wherein at least an insertable length of the hydrophilic coating of the catheter is not in contact with the wetting fluid;
   sterilizing the catheter package with the catheter and the wetting fluid by radiation sterilization while the catheter package is kept in a condition in which at least said insertable length of the hydrophilic coating of the catheter is not in contact with the wetting fluid,
   transferring the catheter package with the catheter and the wetting fluid into a second condition wherein the wetting fluid is in contact with at least the insertable length of the hydrophilic coating of the catheter thereby activates at least the insertable length of the hydrophilic coating of the catheter via gravity and/or inertia,
   wherein the catheter and the wetting fluid are arranged in the catheter package such that there is a free-flow communication between the catheter and the wetting fluid in the first condition and in the second condition, wherein the wetting fluid is a saline solution or liquid water, such that said saline solution or liquid water can freely flow to contact at least the insertable length of the hydrophilic coating of the catheter in the first condition and in the second condition.

2. The method according to claim 1, wherein the activation of the hydrophilic coating of the catheter is done after sterilization of the catheter assembly and before shipment to a user.

3. The method according to claim 1, wherein at least said insertable length of the hydrophilic coating of the catheter and the wetting fluid are separated via force of gravity when in the first condition.

4. The method according to claim 1, wherein at least the insertable length of the hydrophilic coating of the catheter is activated by turning the package with the wetting fluid and the catheter with the hydrophilic coating around an angle of at least 90°.

5. The method according to claim 1, wherein a compartment for the wetting fluid is arranged in the catheter package, which is in direct fluid communication with the hydrophilic coating of the catheter.

6. The method according to claim 5, wherein at least the hydrophilic coating of the catheter is surrounded by a sleeve which is combined with the compartment and directs the wetting fluid from the compartment to the hydrophilic coating of the catheter.

7. The method according to claim 1, wherein the activation of the hydrophilic coating of the catheter is done after sterilization of the catheter assembly and before shipment to a user, and
wherein at least said insertable length of the hydrophilic coating of the catheter and the wetting fluid are separated via force of gravity when in the first condition.

8. The method according to claim 7, wherein at least the insertable length of the hydrophilic coating of the catheter is activated by turning the package with the wetting fluid and the catheter with the hydrophilic coating around an angle of at least 90°.

9. The method according to claim 1, wherein at least said insertable length of the hydrophilic coating of the catheter and the wetting fluid are separated via force of gravity when in the first condition, and
wherein at least the insertable length of the hydrophilic coating of the catheter is activated by turning the package with the wetting fluid and the catheter with the hydrophilic coating around an angle of at least 90°.

10. The method according to claim 1, wherein the activation of the hydrophilic coating of the catheter is done after sterilization of the catheter assembly and before shipment to a user, and
wherein at least the insertable length of the hydrophilic coating of the catheter is activated by turning the package with the wetting fluid and the catheter with the hydrophilic coating around an angle of at least 90°.

* * * * *